United States Patent [19]

Murphy

[11] 4,023,568

[45] May 17, 1977

[54] CAST POSITIONING DEVICE

[76] Inventor: Jack Murphy, 25361 Yale St., Hemet, Calif. 92343

[22] Filed: Feb. 9, 1976

[21] Appl. No.: 656,438

[52] U.S. Cl. .................................. 128/83; 128/94
[51] Int. Cl.² ........................................ A61F 5/04
[58] Field of Search ............ 128/83, 84 R, 84 C, 128/94, 87, 90, 91; 224/11, 12, 22, 5

[56] References Cited

UNITED STATES PATENTS

| 2,856,919 | 10/1958 | Murray | 128/90 |
| 3,706,310 | 12/1972 | Garnett | 128/94 |
| D200,752 | 3/1965 | Hill | 128/94 X |

FOREIGN PATENTS OR APPLICATIONS 260,480  6/1913  Germany ..................... 128/94

*Primary Examiner*—John D. Yasko
*Attorney, Agent, or Firm*—John Joseph Hall

[57] ABSTRACT

A cast positioning device for embedding in a cast of a person's limb and having a center portion with an eye member through which a cord can be run to secure the limb in a desired position of elevation or rotation or under traction.

2 Claims, 8 Drawing Figures

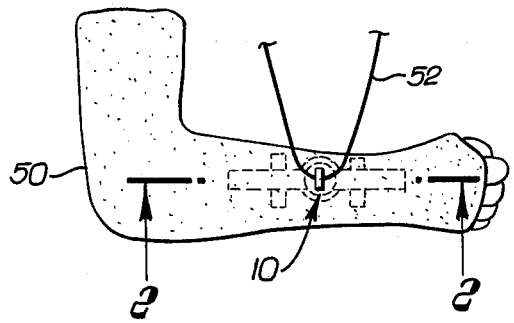
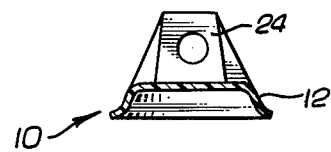
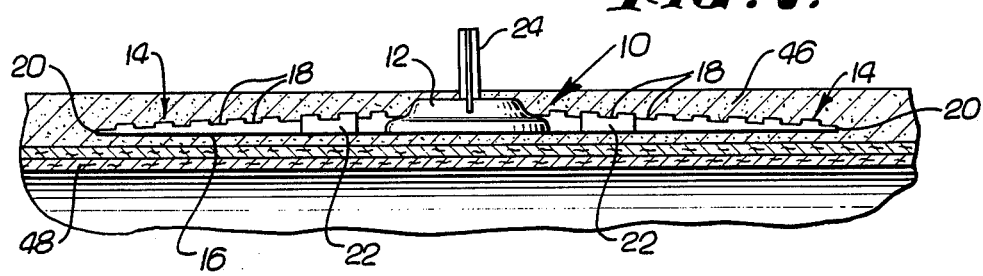
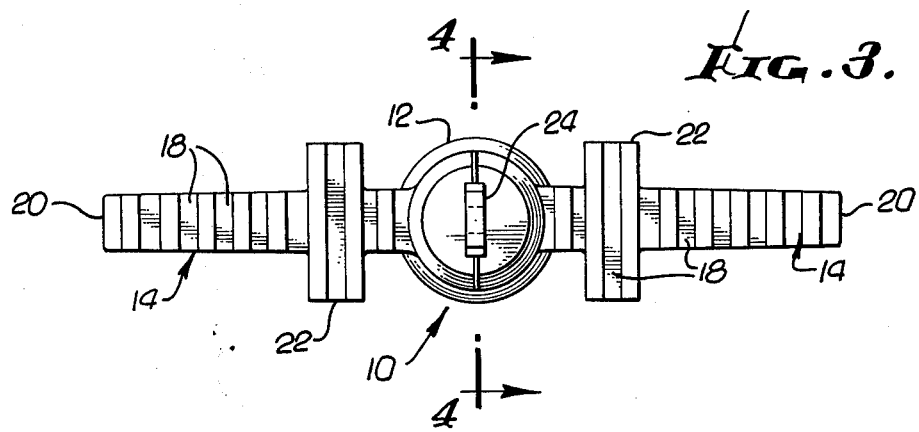

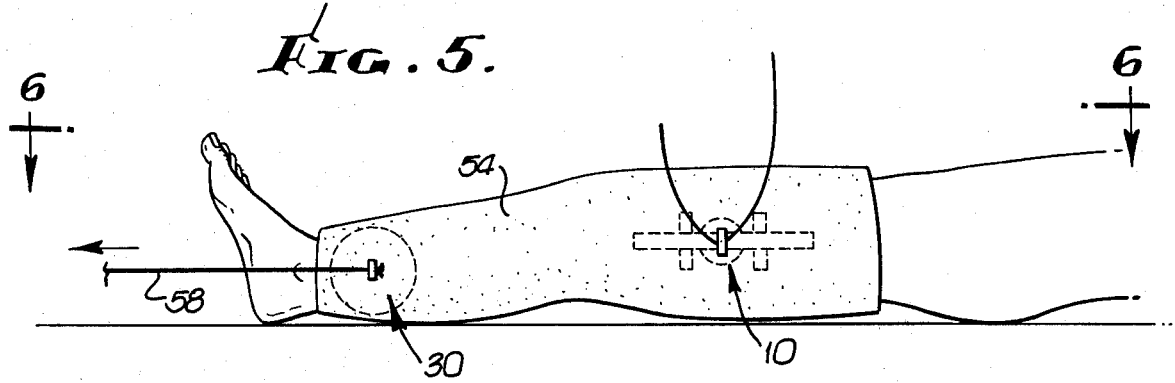
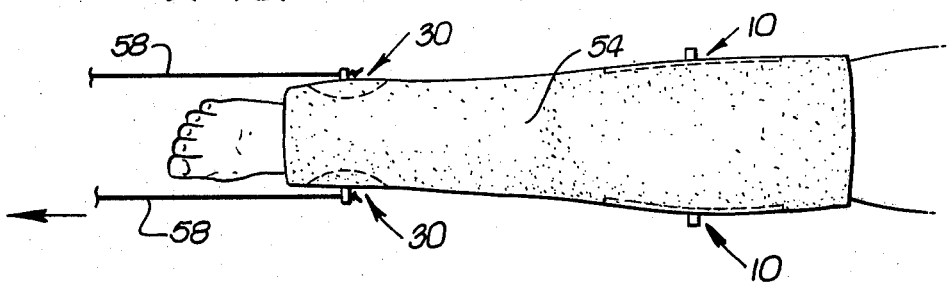
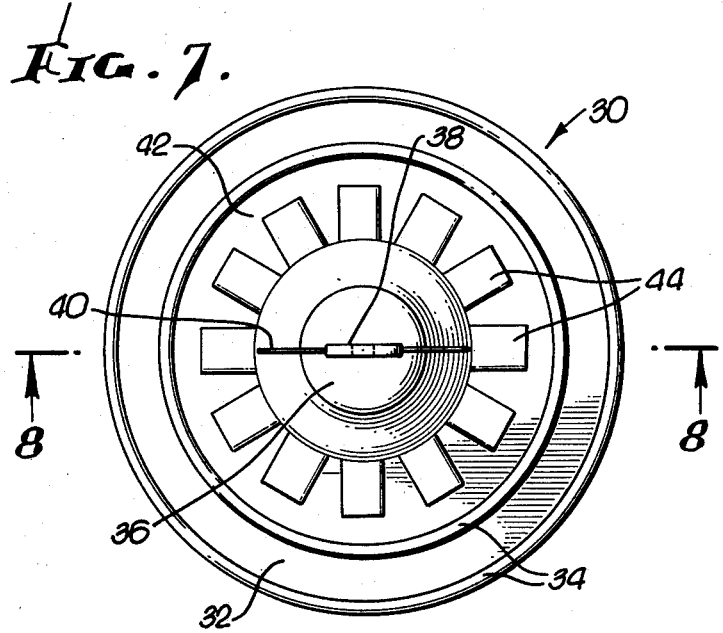
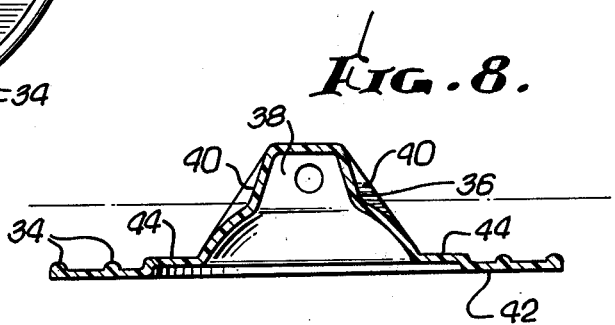

CAST POSITIONING DEVICE

BACKGROUND OF THE INVENTION

This invention pertains to the field of casts for fractured limbs of a person and provides improvements for maintaining a limb in a cast at a desired position, elevation, and rotation.

SUMMARY OF THE INVENTION

The cast positioning device has a center portion formed into an eye member through which a cord can be run. One embodiment of the cast positioning device has a pair of strap members on each side of the center portion so that the cast positioning device can be embedded in the cast plaster while wet with the eye member above the surface of the plaster. Another embodiment of the cast positioning device has a disk member around the base of a center portion which is imbedded in the cast plaster while wet with the eye member above the surface of the plaster. This embodiment is preferred for use in conjunction in traction of a person's limb and may be used instead of placing a pin through a person's ankle bone, for purposes of traction.

It is, therefore, an object of this invention to provide a cast positioning device which is relatively simple to install in a cast for a person's limb.

Another object of the invention is to provide a cast positioning device which easily maintains a person's limb in a cast at the desired position, elevation, and rotation.

A further object of this invention is to provide a cast positioning device which is relatively inexpensive.

A still further object of this invention is to provide a cast positioning device which causes no obstruction for x-rays or other observation of the limb being treated in a cast.

A yet further object of this invention is to provide a cast positioning device which can be used to maintain traction of a person's limb instead of the conventional use of a pin through the person's ankle bone.

These and other objects will be more readily understood by reference to the accompanying claims and drawings, in which:

FIG. 1 is a view in partial section of an embodiment of the invention in place embedded in a cast on the limb of a person.

FIG. 2 is an enlarged view of a section of the apparatus of FIG. 1 taken along line 2—2 of FIG. 1.

FIG. 3 is a top plan view of an embodiment of the invention.

FIG. 4 is a section taken along line 4—4 of FIG. 3.

FIG. 5 is a view in partial section of an embodiment of the invention in place embedded in the ankle area of a cast on the leg of a person under traction, and another embodiment of the invention in place embedded in the thigh area of said cast.

FIG. 6 is a section taken along line 6—6 of FIG. 5.

FIG. 7 is a top plan view of another embodiment of the invention.

FIG. 8 is a view taken along line 8—8 of FIG. 7. With reference to the drawings, one embodiment 10 of the cast positioning device has a circular center portion 12 with two longitudinal strap members 14 extending outwardly in the same plane as said center portion 12 and on each side of said center portion 12. The strap members 14 are preferably formed with a flat bottom 16 and a plurality of recesses 18 formed in their top surfaces. Strap members 14 are preferably tapered in thickness toward their outer ends 20. Each strap member 14 has an anchor member 22 formed at right angles to its inner end.

The center portion 12 is formed with an eye member 24 at its top and concentric circular ridges 28, said eye member 24 having tapered sides with a web around the sides.

The embodiment 10 of the cast positioning device is preferably formed in a single piece from any suitable plastic or other material having the requisite strength and resiliency to maintain the cast in the desired position with or without traction.

Another embodiment 30 of the cast positioning device has a disk body 32 with concentric circular ridges 34 at its edges. The center portion 36 of embodiment 30 is formed into an eye member 38 which has tapered sides with a web 40.

The base 42 of the embodiment 30 is formed into a plurality of flanges 44 radiating outwardly from the center circumference of the eye member 38. The embodiment 30 of the cast positioning device is preferably formed in a single piece from any suitable plastic or other material having the requisite strength and resiliency to maintain the cast in the desired position with or without traction.

In operation, the embodiment 10 of the cast positioning device is placed in the position shown in FIG. 2 in plaster 46 while wet over cotton 48 while a cast 50 such as shown in FIG. 1 is being applied to a person's limb. The center portion 12 of the embodiment 10 is situated in the wet plaster 46 so that the eye member 24 is above the top surface of the plaster and the ridges 28 are below the surface of the wet plaster.

After the wet plaster 46 of the cast 50 has dried, embodiment 10 is firmly imbedded in the cast 50 by means of the strap members 14 and anchor members 22. A cord 52 made of any suitable material such as nylon and the like is then run through eye member 24 so that the cast 50 with the limb may be secured in the desired position.

Similarly, the embodiment 30 of the cast positioning device may be embedded in wet plaster over cotton while a cast 54 is being applied to a person's limb. The center portion 36 of embodiment 30 is situated in plaster 56 while wet so that the eye member 38 is above the surface of the plaster 56 and the center portion 36 is below the surface of the plaster 56, thereby firmly embedding the embodiment 30 in the cast when it is dry.

The embodiment 30 may be located at the ankle area of the cast 54 so that a cord 58 of any suitable material such as nylon and the like is run through the eye member 38 and attached to traction if desired, at the desired position. Embodiment 30 may be used at various locations on the cast 54, such as the knee, hip, or groin. The embodiment 10 of the cast positioning device may be also used in conjunction with embodiment 30 as shown in FIG. 5.

Embodiment 30 provides a much superior means of applying traction to a person's limb than the use of a pin inserted through a person's ankle bone.

In this manner, a cast equipped with a cast positioning device of the present invention may be readily placed and anchored and maintained in the desired position, elevation, and rotation. The position, elevation, or rotation of the limb to be treated may be easily modified as desired by use of the cast positioning device. Traction may be easily applied as desired to the limb being treated by the use of embodiment 30 of the cast positioning device, in place of a pin being applied through a person's ankle bone.

The cast positioning device can be added to existing casts applied to a person's limb. This may be done by placing the cast positioning device in position on the cast and sticking it in place with casting plaster bandages. After drying, the cast positioning device is capable of being used in the same manner as described above. Thus, my invention can be used to position both a new cast as well as a pre-existing cast which requires relocation due to a change in a patient's condition.

Although I have described my invention in detail with reference to the accompanying drawings illustrating preferred forms of my invention, it is understood that numerous changes in the details of construction and arrangement of parts may be made without departing from the spirit and scope of the invention as hereinafter claimed.

I claim:

1. A cast positioning device for embedding in a cast applied to a person's limb, comprising:

a substantially rigid and planar center portion having an eye member extending upwardly therefrom;

substantially planar and rigid strap members connected to and in the same plane as said center portion for securing said center portion to a cast by embedding the same in a cast; and integral anchor members extending laterally from said strap members adjacent said center portion.

2. A cast positioning device according to claim 1 in which said strap members have a taper toward their outer ends.

* * * * *